United States Patent [19]

Suzuki et al.

[11] 4,432,908

[45] Feb. 21, 1984

[54] CRYSTAL OF ENANTIOMER PAIR OF PHENYLACETIC ACID ESTER DERIVATIVE AND PROCESS FOR OBTAINING A MIXTURE OF STEREOISOMERS OF THE DERIVATIVE

[75] Inventors: Yukio Suzuki; Masahiro Hayashi, both of Osaka; Kenzi Takuma, Nara, all of Japan

[73] Assignee: Sumitomo Chemical Company, Limited, Osaka, Japan

[21] Appl. No.: 326,317

[22] Filed: Dec. 1, 1981

[30] Foreign Application Priority Data

Dec. 2, 1980 [JP]  Japan .................................. 55-170473

[51] Int. Cl.$^3$ .......................................... C07C 121/75
[52] U.S. Cl. ................................................ 260/465 D
[58] Field of Search ..................................... 260/465 D

[56] References Cited

U.S. PATENT DOCUMENTS

| 4,133,826 | 1/1979 | Warnant et al. | 260/465 D |
|---|---|---|---|
| 4,238,406 | 12/1980 | Suzuki et al. | 260/465 D |
| 4,279,924 | 7/1981 | Suzuki et al. | 424/304 |
| 4,293,504 | 10/1981 | Suzuki et al. | 260/465 D |
| 4,312,816 | 1/1982 | Aketa et al. | 260/465 D |
| 4,321,212 | 3/1982 | Suzuki et al. | 260/465 D |

FOREIGN PATENT DOCUMENTS

| 2289 | 8/1979 | European Pat. Off. |
|---|---|---|
| 1549462 | 8/1979 | United Kingdom. |
| 2014137 | 8/1979 | United Kingdom. |
| 1560303 | 2/1980 | United Kingdom. |

*Primary Examiner*—Dolph H. Torrence
*Attorney, Agent, or Firm*—Sughrue, Mion, Zinn, Macpeak and Seas

[57] ABSTRACT

A crystal of an enantiomer pair of stereoisomers of α-cyano-3-phenoxybenzyl 2-(4-chlorophenyl)isovalerate (general name: fenvalerate) comprising (S)-α-cyano-3-phenoxybenzyl (S)-2-(4-chlorophenyl)isovalerate and an enantiomer thereof, which has the crystal characteristics as specified in the specification, is disclosed. A process for preparing the enantiomer pair or the fenvalerate rich in the enantiomer pair by depositing the above-described crystal from a solution of a racemate of fenvalerate is also disclosed. A process for preparing the enantiomer pair by depositing the crystal from a solution of the fenvalerate rich in the enantiomer pair is further disclosed.

42 Claims, 4 Drawing Figures

CRYSTAL OF ENANTIOMER PAIR OF PHENYLACETIC ACID ESTER DERIVATIVE AND PROCESS FOR OBTAINING A MIXTURE OF STEREOISOMERS OF THE DERIVATIVE

This invention relates to a process for obtaining stereoisomers of α-cyano-3-phenoxybenzyl 2-(4-chlorophenyl)isovalerate (general name: fenvalerate) having an excellent insecticidal and/or acaricidal activity.

As is disclosed in U.S. Pat. No. 4,062,968, fenvalerate is useful as an insecticide and/or acaricide that has a low toxicity to mammals, and that has a residual effect to a moderate extent under the condition for agricultural application, the latter being unsatisfactory in conventional pyrethroid-type insecticides.

Fenvalerate has one asymmetric carbon atom on each of the acid and alcohol moieties, and therefore, four optical isomers are available.

These optical isomers are hereunder referred to as shown in Table 1 below.

TABLE 1

Abbreviations for Optical Isomers

| Alcohol Moiety | Acid Moiety | | |
|---|---|---|---|
| | (S)-Configuration | Racemic | (R)-Configuration |
| (S)-Configuration | Aα-Isomer | α-Isomer | Bα-Isomer |
| Racemic | A-Isomer | "Racemate" | B-Isomer |
| (R)-Configuration | Aβ-Isomer | β-Isomer | Bβ-Isomer |

Combinations of the Aα-isomer and the Bβ-isomer and of the Aβ-isomer and the Bα-isomer are each in a relationship of enantiomer pair. The enantiomer pair of the Aα-isomer and the Bβ-isomer is referred to as a Y-isomer, and the enantiomer pair of the Aβ-isomer and the Bα-isomer as an X-isomer.

According to the disclosures of U.S. Pat. Nos. 4,176,195 and 4,238,406, the insecticidal and/or acaricidal efficacy of the Y-isomer of fenvalerate is about twice as high as that of racemic fenvalerate ("racemate") [the ratio of X-isomer to Y-isomer is about 1:1 (however, the ester having a ratio of X-isomer to Y-isomer of from 60/40 to 45/55 will be hereunder referred to as a racemate)], and the Y-isomer (the ester containing, in general, at least 92% of the Y-isomer) or the ester rich in the Y-isomer (the ester containing, in general, more than 60% but less than 92% of the Y-isomer, which will be hereunder referred to as a Y-rich isomer) can be obtained by crystallizing the Y-isomer out of racemic fenvalerate in the presence or absence of a base. The thus-obtained crystal of the Y-isomer (hereunder referred to as a I-type crystal) has a melting point of 40° C., and its infrared absorption spectrum (by a KBr method) and powder X-ray diffraction spectrum (Cu-K$_\alpha$) are given in FIGS. 1 and 2, respectively.

As the result of further extensive studies, the present inventors reached novel findings that the X-isomer of fenvalerate crystallizes (m.p. 63°–66° C.), and besides that even the racemic fenvalerate can solidify (m.p. 37.0°–53.6° C.). The present inventors made further studies on the basis of this novel fact, and found that by crystallizing the X-isomer (the ester containing, in general, at least 92% of the X-isomer) or the ester rich in the X-isomer (the ester containing, in general, more than 60% but less than 92% of the X-isomer, which will be hereunder referred to as an X-rich isomer) from the racemate and removing the resulting crystal, the Y-rich isomer can be obtained.

As the result of still further extensive studies, the inventors found that there is a crystal different from the known I-type crystal (this crystal will be referred to as a II-type crystal), and that the rate of crystallization of the II-type crystal from a solution of the racemate is faster than that of the known I-type crystal, and thus, they achieved the present invention.

The II-type crystal of the Y-isomer according to the present invention has the following characteristics:

| Hue: | colorless |
|---|---|
| Melting Point: | 48.2 to 52.0° C. |
| Crystal System*: | monoclinic |
| Lattice Constant*: | a = 11.90 Å, b = 5.60 Å, c = 32.58 Å, β = 93.0° |
| Space Group*: | P$_2$ 1/c |
| Density: | 1.28 g/cm$^3$ |
| Number of Molecules in Unit Lattice*: | 4 |

*the data obtained by X-ray diffractometry

An infrared absorption spectrum and a powder X-ray diffraction spectrum (Cu-K$_\alpha$) of the II-type crystal of the Y-isomer are given in FIGS. 3 and 4, respectively.

An object of the present invention is, therefore, to provide a crystal of a Y-isomer of fenvalerate having the characteristics as specified above (i.e., a II-type crystal).

Another object of the present invention is to provide a process for preparing a Y-isomer or Y-rich isomer of fenvalerate by depositing a II-type crystal of a Y-isomer of fenvalerate from a solution of a racemate of fenvalerate.

Further object of the present invention is to provide a process for preparing a Y-isomer of fenvalerate by depositing a II-type crystal of a Y-isomer of fenvalerate from a solution of a Y-rich isomer of fenvalerate.

Figure 1:
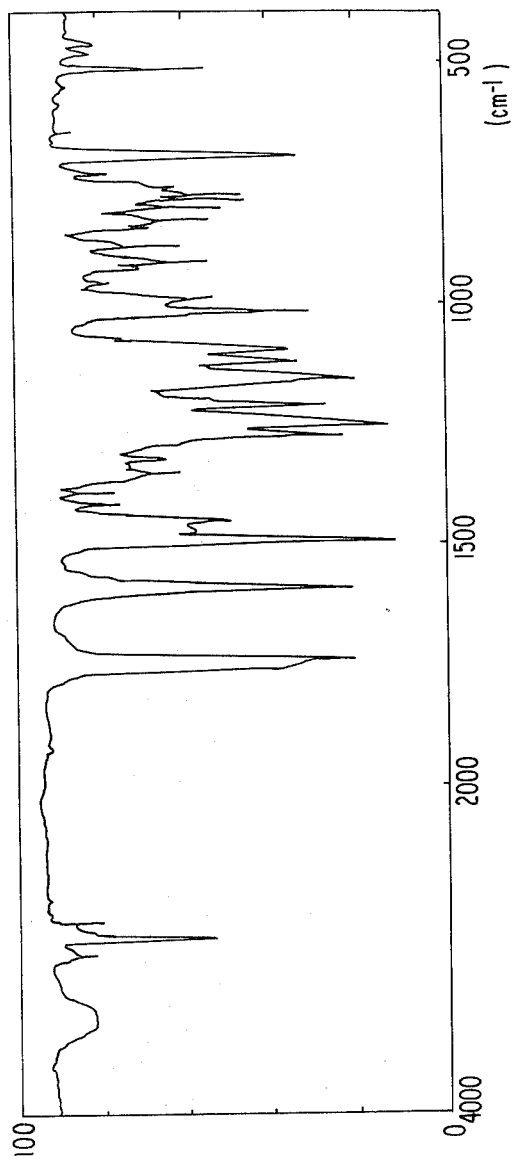
FIG. 1 is an infrared absorption spectrum of a known I-type crystal of Y-isomer of fenvalerate according to a KBr method.
Figure 2:
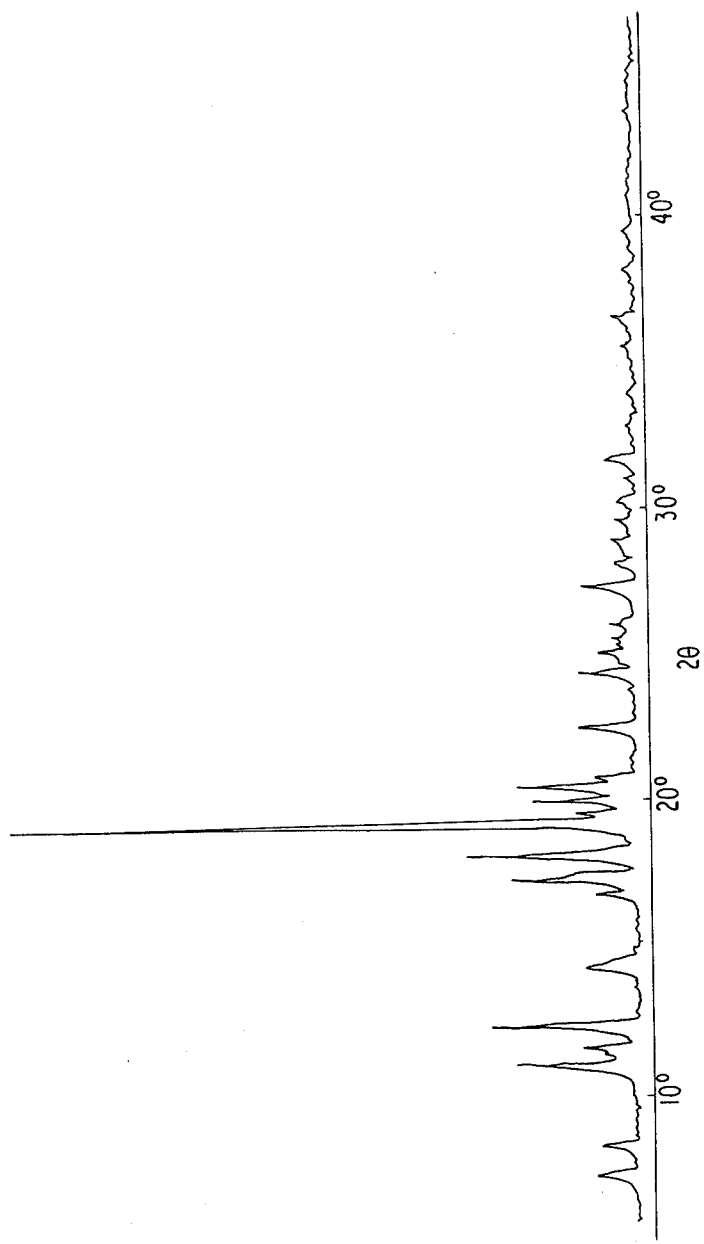
FIG. 2 is a powder X-ray diffraction spectrum (Cu-K$_\alpha$) of a known I-type crystal of Y-isomer of fenvalerate.

The II-type crystal of Y-isomer of fenvalerate can, for example, be easily prepared by seeding a solution of a racemate or Y-rich isomer of fenvalerate with a II-type crystal of a Y-isomer of fenvalerate. In depositing the II-type crystal of Y-isomer of fenvalerate, it is not essential but preferred that the II-type crystal is present in the system. However, since if a crystal of an X-isomer, X-rich isomer, racemate, A-isomer or B-isomer is present in the system, a crystal of an X-rich isomer is likely formed, attention such that such a crystal is not substantially present in the system must be paid. For this purpose, it is preferred that the starting solution of racemate or Y-rich isomer of fenvalerate is pre-heated at a temperature of 40° C. or higher. More preferably, the system is refluxed using a solvent prior to the crystallization.

In addition, the II-type crystal of Y-isomer which can be used as a seed crystal must be substantially free of a crystal of an X-isomer, X-rich isomer, racemate, A-isomer or B-isomer of fenvalerate. For this purpose, it is preferred that the II-type crystal obtained by recrystallization from a solvent is used. It is more preferred to use the II-type crystal obtained by recrystallization being not isolated but mixed with the starting solution together with the mother liquor.

The solvent used for the recrystallization of the seed crystal may be the same as or different from the solvent used for the formation of the II-type crystal from the solution of racemate or Y-rich isomer. Examples of the solvent which can be used for the recrystallization are alcohols, aliphatic or alicyclic hydrocarbons or mixtures thereof. These solvents may also be mixed with aromatic hydrocarbons, ketones, esters, ethers, chlorinated hydrocarbon solvents and phenols. Preferred examples are alcohols which are used alone or in combination with aliphatic hydrocarbons and/or aromatic hydrocarbons. Preferred alcohols are those having 1 to 5 carbon atoms, such as methanol, ethanol, n-propanol, isopropanol and n-butanol. Preferred aliphatic or alicyclic hydrocarbons are those having 5 to 12 carbon atoms, such as hexane, heptane, octane, petroleum ether, ligroin and methylcyclohexane. Preferred aromatic hydrocarbons are benzene, toluene and xylene. The optimum amount of the solvent varies with the type of solvent, but generally, it is used in a weight of 0.5 to 50 times, preferably at least 5 times, as great as that of the Y-isomer. To prevent the denaturation or deterioration of the Y-isomer, a small amount (e.g., less than 5% of the solvent) of acetic acid may be added to the solvent.

Examples of the solvent which can be used for the deposition of the II-type crystal from the solution of racemate or Y-rich isomer are alcohols, aliphatic hydrocarbons, alicyclic hydrocarbons and mixed solvents thereof. Mixed solvents consisting of these solvents and aromatic hydrocarbons, ketones, esters, ethers, chlorinated hydrocarbon solvents and phenols can also be used. Preferred examples are alcohols alone or in admixture with aliphatic hydrocarbons and/or aromatic hydrocarbons. Preferred alcohols are those having 1 to 5 carbon atoms, such as methanol, ethanol, n-propanol, isopropanol and n-butanol. Preferred aliphatic and alicyclic hydrocarbons are those having 5 to 12 carbon atoms, such as hexane, heptane, octane, petroleum ether, ligroin and methylcyclohexane. Examples of the aromatic hydrocarbons are benzene, toluene and xylene. The optimum amount of the solvent used varies with the type thereof and the crystallization temperature, and therefore, can not be unequivocally defined. But, generally the solvent is used in a weight 0.5 to 30 times as great as that of the starting racemate or Y-rich isomer.

In the procedure for obtaining the Y-isomer or Y-rich isomer from the solution of racemate, the use of a basic catalyst is not essential. When the crystallization and isolation of the II-type crystal of Y-isomer has been performed in the absence of a basic catalyst, the ester is recovered from the mother liquor, and the residual ester in the mother liquor which is rich in the X-isomer is brought into contact with a basic catalyst to subject to epimerization on the alcohol moiety to restore the ratio of the X-isomer to Y-isomer to an equilibrium, and thereafter, the crystallization is again carried out whereby the racemate can be converted to the Y-isomer almost quantitatively. Crystallization and isolation of the Y-isomer can also be performed in the presence of a basic catalyst, and the advantage of this method is that the II-type crystal of Y-isomer can be obtained in an amount greater than that of the Y-isomer initially contained in the racemate (usually about 50%). The ester in the mother liquor is recovered and put to further use after purification, if desired.

Alternatively, after the II-type crystal of Y-isomer has deposited from the solution of racemate in the presence of a basic catalyst, the basic catalyst may be removed or made inert (neutralized) without separating the resulting crystal from the mother liquor, and not only the II-type crystal of Y-isomer but also the racemate in the mother liquor can be recovered by concentrating all the mother liquor or by other means, whereby the Y-rich isomer can be obtained. In this case, the residual Y-isomer in the mother liquor can be used effectively without being lost. The simplicity of this procedure makes it an economically advantageous method that is adapted to industrial production of the desired isomer.

Examples of the basic catalyst which can be used for the crystallization include nitrogen-containing bases such as ammonia, hydrazine, methylamine, ethylamine, n-propylamine, isopropylamine, n-butylamine, dimethylamine, diethylamine, di-n-propylamine, di-n-butylamine, trimethylamine, triethylamine, cyclohexylamine, ethylenediamine, ethanolamine, pyrrolidine, piperidine, morpholine, aniline, 1-naphthylamine, pyridine, quinoline and 1,5-diazabicyclo[4,3,0]-non-5-ene; phosphorus-containing bases such as triphenylphosphine and tri-n-butylphosphine; quaternary ammonium hydroxides such as tetramethylammonium hydroxide and tetra-n-butylammonium hydroxide; and metal-containing bases such as sodium hydroxide, potassium hydroxide, sodium carbonate, sodium cyanide, sodium methylate, sodium hydride and sodium amide. The amount of the basic catalyst used varies with the type of the catalyst and solvent, their amount and the crystallization temperature, but it is used generally in an amount of 0.001 to 200 mol% per mol of the starting ester, and when ammonia or triethylamine is, for example, used, it is generally used in an amount of 5 to 100 mol% per mol of the starting ester.

On the other hand, in the procedure for obtaining the Y-isomer from the solution of Y-rich isomer, the use of a basic catalyst is not required, but the use of a small amount of an acidic catalyst such as acetic acid, etc., is rather desired from the reason that the occurrence of epimerization can be prevented, especially when a protonic solvent, e.g., alcohol, is used. In this case, if desired, after the formation and isolation of the II-type crystal of Y-isomer, the ester is recovered from the mother liquor and brought into contact with a basic catalyst to subject it to epimerization on the alcohol moiety, whereby the resulting ester may be reused as a starting material in the crystallization procedure. In this procedure, the Y-rich isomer which can be used as the starting material can be obtained by not only the method as described above but also a method that a crystal of the X-rich isomer is formed from the racemate and then removed off to obtain the Y-rich isomer from the mother liquor.

In the present invention, the formation of the II-type crystal of Y-isomer from the solution of racemate is generally conducted at a temperature of 25° C. or lower, preferably between −30° C. and 10° C. Further-more, the formation of the II-type crystal of Y-isomer from the solution of Y-rich isomer is generally conducted at a temperature of 35° C. or lower, preferably between −30° C. and 25° C.

The present invention can be proceeded in any of a batch manner, semi-continuous manner and continuous manner. In this case, the employment of stirring in the system is not essential. For example, a method that a crystal is grown by circulating the starting solution of racemate or Y-rich isomer may be employed.

This invention is now described in greater detail by reference to the following Examples which are given here for illustrative purposes only and are by no means intended to limit its scope. In the Examples, the term "X/Y" means a ratio of X-isomer to Y-isomer.

EXAMPLE 1

5 g of a crystal of a Y-isomer of fenvalerate (a I-type crystal of X/Y=3.8/96.2, m.p.: 37.0°–41.8° C.) was dissolved in 10 g of methanol under heating, and the mixture was cooled to room temperature (i.e., 20° to 25° C.), followed by seeding with 1 mg of a crystal of a racemate of fenvalerate (X/Y=50/50, m.p.: 37.0°–53.6° C.). The resulting mixture was allowed to stand for one day and subjected to filtration to obtain 2.98 g of a needle-like crystal of a Y-isomer of fenvalerate (II-type crystal).

Figure 3:
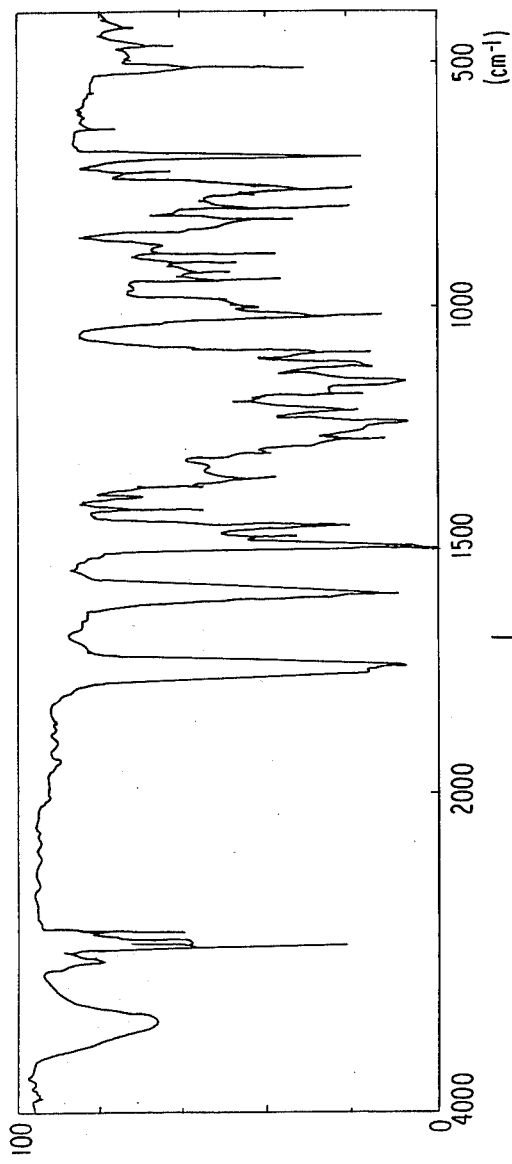
FIG. 3 is an infrared absorption spectrum of a II-type crystal of Y-isomer of fenvalerate of the present invention according to a KBr method.

The thus-obtained crystal was found to have an X/Y of 0.4/99.6 and a melting point of 48.5° to 50.0° C. An infrared absorption spectrum of this crystal according to a KBr method is illustrated in FIG. 3.

EXAMPLE 2

200 g of the crystal of Y-isomer of fenvalerate as used in Example 1 was dissolved in 600 g of heptane under heating. After seeding with 1 mg of the same crystal of racemate of fenvalerate as in Example 1 at 30° C., the mixture was gradually cooled to 15° C. over a period of time of 2 hours under stirring to obtain a crystal of a Y-isomer of fenvalerate (II-type crystal) which was subsequently collected by filtration. The thus-collected crystal (171 g) was found to have an X/Y of 0.2/99.8 and a melting point of 48.2° to 52.0° C.

Figure 4:
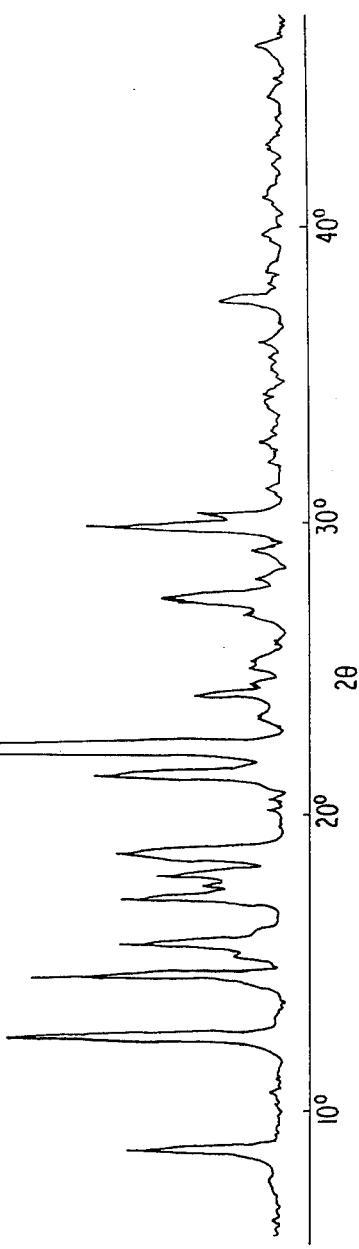
FIG. 4 is a powder X-ray diffraction spectrum (Cu-K$_\alpha$) of a II-type crystal of Y-isomer of fenvalerate of the present invention.

An infrared absorption spectrum of this crystal according to a KBr method was substantially the same as that of the crystal obtained in Example 1, and a powder X-ray diffraction spectrum (Cu-K$_\alpha$) of the crystal is illustrated in FIG. 4.

EXAMPLE 3

2 g of the crystal of Y-isomer of fenvalerate as used in Example 1 was dissolved in 40 g of heptane under heating, and the mixture was cooled to 20.5° C., followed by seeding with 1 mg of the II-type crystal of Y-isomer of fenvalerate obtained in Example 1. The resulting mixture was allowed to stir for 3 hours at 20.5° to 22° C., whereupon a crystal of a Y-isomer of fenvalerate (II-type crystal) deposited, which mixture was in a slurry state as a whole.

Individually, 80 g of a racemate of fenvalerate having an X/Y of 50/50 was dissolved in a mixture of 40 g of heptane and 80 g of methanol, followed by refluxing for 30 minutes and then cooling to −18° C. Thereafter, to this solution was added the II-type crystal of Y-isomer of fenvalerate prepared as above together with the mother liquor at −18° C. The resulting mixture was allowed to stir for 2 hours at −18° C. as it was, and then subjected to filtration. Thus, 24.95 g of a crystal of a Y-isomer of fenvalerate (II-type crystal) that was found to have an X/Y of 7.6/92.4 was obtained.

An infrared absorption spectrum of this crystal was substantially the same as that of the crystal obtained in Example 1.

EXAMPLE 4

To 10 g of the crystal of Y-isomer of fenvalerate as used in Example 1 were added 27 g of heptane and 3 g of toluene, and the mixture was refluxed for 30 minutes. The resulting mixture was cooled to 25° C. and seeded with 1 mg of the II-type crystal of Y-isomer of fenvalerate obtained in Example 2, followed by stirring it for 1 hour at the same temperature, whereupon a crystal of a Y-isomer of fenvalerate (II-type crystal) deposited, which mixture was in a slurry state as a whole.

Individually, to 50 g of a racemate of fenvalerate having an X/Y of 53.2/46.8 was added 250 g of methanol, and the mixture was refluxed for 30 minutes and then cooled to −15° C. Thereafter, to this solution was added the II-type crystal of Y-isomer of fenvalerate prepared as above together with the mother liquor at −15° C., and 7.86 g of a 12.9% ammonia/methanol solution was further added thereto, followed by allowing the mixture to stir for 62 hours at the same temperature. To the resulting mixture was added 4.29 g of acetic acid, followed by subjecting it to filtration to obtain 37.98 g of a crystal of a Y-isomer of fenvalerate (II-type crystal) that was found to have an X/Y of 0.7/99.3.

An infrared absorption spectrum of the crystal was substantially the same as that of the crystal obtained in Example 1.

EXAMPLE 5

50 g of a racemate of fenvalerate having an X/Y of 53.7/46.3 was dissolved in a mixture of 50 g of methanol and 50 g of heptane, and the solution was refluxed for 30 minutes, followed by cooling to −3° C.

Individually, a mixture of 2 g of a Y-isomer of fenvalerate having an X/Y of 0.6/99.4, 14.93 g of methanol and 0.07 g of acetic acid was refluxed for 30 minutes, and then cooled to 15° C. After seeding with 1 mg of a II-type crystal of a Y-isomer of fenvalerate having an X/Y of 0.3/99.7, the resulting mixture was allowed to stir for 30 minutes, whereupon a crystal of a Y-isomer of fenvalerate (II-type crystal) deposited, which mixture was in a slurry state as a whole.

The racemate solution that had been prepared above was seeded with about 1 cc of the slurry thus obtained, and at the same time, 1 cc of a 28% aqueous ammonia solution was added thereto. The resulting mixture was allowed to stir for 20 hours at −3° C., followed by subjecting it to filtration to obtain 39.78 g of a crystal of a Y-isomer of fenvalerate (II-type crystal) that was found to have an X/Y of 3.9/96.1.

EXAMPLE 6

200 g of a racemate of fenvalerate having an X/Y of 53.4/46.6 was dissolved in a mixture of 199 g of methanol and 1 g of acetic acid. After seeding with 0.5 g of a crystal of a racemate of fenvalerate having an X/Y of 51.8./48.2 at 30° C., the mixture was allowed to stir for 2 hours at 30° C., for 5 hours in a region of 30° C. to 15° C. with cooling, and for one hour at 15° C., respectively. The resulting crystal of X-rich isomer of fenvalerate was filtered off, and the mother liquor was concentrated to obtain 88.16 g of fenvalerate rich in the Y-isomer that was found to have an X/Y of 31.5/68.5.

50.1 g of the thus-obtained fenvalerate rich in the Y-isomer was dissolved in a mixture of 49.75 g of methanol, 0.25 g of acetic acid and 50 g of heptane, and the solution was refluxed for 70 minutes. Thereafter, the resulting solution was cooled to 5° C., and seeded with 1 mg of a II-type crystal of a Y-isomer of fenvalerate having an X/Y of 0.2/99.8. The mixture was allowed to stir for 4 hours at the same temperature. The resulting crystal was collected by filtration to obtain 12.32 g of a crystal of a Y-isomer of fenvalerate (II-type crystal) that was found to have an

EXAMPLE 7

25 g of fenvalerate rich in the Y-isomer having an X/Y of 13.9/86.1 was dissolved in 50 g of methanol, and the solution was seeded with 1 mg of the II-type crystal of Y-isomer of fenvalerate obtained in Example 1 at 20° C. The mixture was allowed to stir for 4 hours at the same temperature, whereupon a crystal of a Y-isomer of fenvalerate (II-type crystal) deposited, which mixture was in a slurry state as a whole, followed by subjecting it to filtration to obtain 8.71 g of a crystal of a Y-isomer of fenvalerate (II-type crystal) that was found to have an X/Y of 0.6/99.4.

While the invention has been described in detail and with reference to specific embodiments thereof, it will be apparent to one skilled in the art that various changes and modifications can be made therein without departing from the spirit and scope thereof.

What is claimed is:

1. A crystal of an enantiomer pair of stereoisomers of α-cyano-3-phenoxybenzyl 2-(4-chlorophenyl)isovalerate comprising (S)-α-cyano-3-phenoxybenzyl (S)-2-(4-chlorophenyl)isovalerate and an enantiomer thereof, said crystal having the following crystal characteristics:

| crystal system | monoclinic |
|---|---|
| lattice constant | a = 11.90 Å, b = 5.60 Å, c = 32.58 Å, β = 93.0° |
| space group | $P2_{1/c}$ |
| density | 1.28 g/cm$^3$ |
| number of molecules in unit lattice | 4 |

2. A process for preparing a mixture of stereoisomers of a α-cyano-3-phenoxybenzyl 2-(4-chlorophenyl)-isovalerate which consists essentially of a Y-isomer that is an enantiomer pair of (S)-α-cyano-3-phenoxybenzyl (S)-2-(4-chlorophenyl)isovalerate and an enantiomer thereof, or which is rich in said Y-isomer, the process comprising depositing a crystal of said Y-isomer from a solution of α-cyano-3-phenoxybenzyl 2-(4-chlorophenyl)isovalerate in the presence or absence of a basic catalyst, said crystal having the following crystal characteristics:

| crystal system | monoclinic |
|---|---|
| lattice constant | a = 11.90 Å, b = 5.60 Å, c = 32.58 Å, β = 93.0° |
| space group | $P2_{1/c}$ |
| density | 1.28 g/cm$^3$ |
| number of molecules in a unit lattice | 4 | wherein the crystallization is carried out in the presence of a crystal of said Y-isomer having said crystal characteristics as a seed crystal.

3. A process according to claim 2, wherein the crystallization is carried out in the absence of a basic catalyst, and the resulting crystal is separated from the mother liquor.

4. A process according to claim 2, wherein the crystallization is carried out in the presence of a basic catalyst, and the resulting crystal is separated from the mother liquor.

5. A process according to claim 2, wherein the crystallization is carried out in the presence of a basic catalyst, and the resulting crystal is recovered together with α-cyano-3-phenoxybenzyl 2-(4-chlorophenyl)-isovalerate contained in the mother liquor.

6. A process according to claim 3, wherein prior to the crystallization, the solution of α-cyano-3-phenoxybenzyl 2-(4-chlorophenyl)isovalerate is heated to a temperature of 40° C. or higher.

7. A process according to claim 4, wherein prior to the crystallization, the solution of α-cyano-3-phenoxybenzyl 2-(4-chlorophenyl)isovalerate is heated to a temperature of 40° C. or higher.

8. A process according to claim 5, wherein prior to the crystallization, the solution of α-cyano-3-phenoxybenzyl 2-(4-chlorophenyl)isovalerate is heated to a temperature of 40° C. or higher.

9. A process according to claim 2, wherein said crystal of Y-isomer that is obtained by recrystallization is used as the seed crystal.

10. A process according to claim 6, wherein prior to the crystallization, the solution of α-cyano-3-phenoxybenzyl 2-(4-chlorophenyl)isovalerate is heated under reflux condition.

11. A process according to claim 7, wherein prior to the crystallization, the solution of α-cyano-3-phenoxybenzyl 2-(4-chlorophenyl)isovalerate is heated under reflux condition.

12. A process according to claim 8, wherein prior to the crystallization, the solution of α-cyano-3-phenoxybenzyl 2-(4-chlorophenyl)isovalerate is heated under reflux condition.

13. A process according to claim 9, wherein said Y-isomer is recrystallized in a solvent, and the resulting crystal is not isolated but mixed with the solution of α-cyano-3-phenoxybenzyl 2-(4-chlorophenyl)-isovalerate as a seed crystal together with the mother liquor.

14. A process according to claim 10, wherein said crystal of Y-isomer that is obtained by recrystallization is used as the seed crystal.

15. A process according to claim 11, wherein said crystal of Y-isomer that is obtained by recrystallization is used as the seed crystal.

16. A process according to claim 12, wherein said crystal of Y-isomer that is obtained by recrystallization is used as the seed crystal.

17. A process according to claim 14, wherein said Y-isomer is recrystallized in a solvent, and the resulting crystal is not isolated but mixed with the solution of α-cyano-3-phenoxybenzyl 2-(4-chlorophenyl)-isovalerate as a seed crystal together with the mother liquor.

18. A process according to claim 15, wherein said Y-isomer is recrystallized in a solvent, and the resulting crystal is not isolated but mixed with the solution of α-cyano-3-phenoxybenzyl 2-(4-chlorophenyl)-isovalerate as a seed crystal together with the mother liquor.

19. A process according to claim 16, wherein said Y-isomer is recrystallized in a solvent, and the resulting crystal is not isolated but mixed with the solution of α-cyano-3-phenoxybenzyl 2-(4-chlorophenyl)-isovalerate as a seed crystal together with the mother liquor.

20. A process according to any of claims 9, 13 or 14 to 19, wherein the seed crystal is obtained by recrystallization from a solvent which is made of one or more solvents selected from alcohols, aliphatic hydrocarbons and alicyclic hydrocarbons, or a solvent containing one or more of these solvents.

21. A process according to claim 20, wherein the recrystallization solvent is used in a weight of from 0.5 to 50 times as great as that of said Y-isomer.

22. A process according to any of claims 9, 13 or 14 to 19, wherein the seed crystal is obtained by recrystallization from a solvent which is made of one or more solvents selected from alcohols, aliphatic hydrocarbons and alicyclic hydrocarbons, or a solvent containing one or more of these solvents, said solvent containing not more than 5% by weight of acetic acid on the basis of the total amount of the solvent used.

23. A process according to claim 22, wherein the crystallization solvent is used in a weight of from 0.5 to 50 times as great as that of said Y-isomer.

24. A process for preparing a Y-isomer that is an enantiomer pair of (S)-α-cyano-3-phenoxybenzyl (S)-2-(4-chlorophenyl)isovalerate and an enantiomer thereof, which comprises depositing a crystal of said Y-isomer from a solution of α-cyano-3-phenoxybenzyl 2-(4-chlorophenyl)-isovalerate that is rich in said Y-isomer, said crystal having the following crystal characteristics:

| | |
|---|---|
| crystal system | monoclinic |
| lattice constant | $a = 11.90$ Å, $b = 5.60$ Å, $c = 32.58$ Å, $\beta = 93.0°$ |
| space group | $P2_1/c$ |
| density | 1.28 g/cm$^3$ |
| number of molecules in unit lattice | 4 | wherein the crystallization is carried out in the presence of a crystal of said Y-isomer having said crystal characteristics as a seed crystal and separating the crystal from the mother liquor.

25. A process according to claim 24, wherein the solution of α-cyano-3-phenoxybenzyl 2-(4-chlorophenyl)-isovalerate contains more than 60% but less than 92% of said Y-isomer.

26. A process according to claim 24, wherein a crystal rich in an X-isomer that is an enantiomer pair of (S)-α-cyano-3-phenoxybenzyl (R)-2-(4-chlorophenyl)-isovalerate and an enantiomer thereof is deposited from the solution of α-cyano-3-phenoxybenzyl 2-(4-chlorophenyl)-isovalerate, and α-cyano-3-phenoxybenzyl 2-(4-chlorophenyl)-isovalerate rich in said Y-isomer obtained from the mother liquor from which the resulting crystal has been removed off is used as the starting material.

27. A process according to claim 24, wherein prior to the crystallization, the solution of α-cyano-3-phenoxybenzyl 2-(4-chlorophenyl)isovalerate is heated to a temperature of 40° C. or higher.

28. A process according to claim 24, wherein said crystal of Y-isomer that is obtained by recrystallization is used as the seed crystal.

29. A process according to claim 27, wherein prior to the crystallization, the solution of α-cyano-3-phenoxybenzyl 2-(4-chlorophenyl)isovalerate is heated under reflux condition.

30. A process according to claim 28, wherein said Y-isomer is recrystallized in a solvent, and the resulting crystal is not isolated but mixed with the solution of α-cyano-3-phenoxy 2-(4-chlorophenyl)-isovalerate as a seed crystal together with the mother liquor.

31. A process according to claim 29, wherein said crystal of Y-isomer that is obtained by recrystallization is used as the seed crystal.

32. A process according to claim 31, wherein said Y-isomer is recrystallized in a solvent, and the resulting crystal is not isolated but mixed with the solution of α-cyano-3-phenoxybenzyl 2-(4-chlorophenyl)isovalerate as a seed crystal together with the mother liquor.

33. A process according to any of claims 28, 30, 31 or 32, wherein the seed crystal is obtained by recrystallization from a solvent which is made of one or more solvents selected from alcohols, aliphatic hydrocarbons and alicyclic hydrocarbons, or a solvent containing one or more of these solvents.

34. A process according to claim 33, wherein the recrystallization solvent is used in a weight of from 0.5 to 50 times as great as that of said Y-isomer.

35. A process according to any of claims 28, 30, 31 or 32, wherein the seed crystal is obtained by recrystallization from a solvent which is made of one or more solvents selected from alcohols, aliphatic hydrocarbons and alicyclic hydrocarbons, or a solvent containing one or more of these solvents, said solvent containing not more than 5% by weight of acetic acid on the basis of the total amount of the solvent used.

36. A process according to claim 35, wherein the recrystallization solvent is used in a weight of from 5 to 50 times as great as that of said Y-isomer.

37. A process according to either of claims 2 or 24, wherein said Y-isomer is crystallized from the solution of α-cyano-3-phenoxybenzyl 2-(4-chlorophenyl)isovalerate, or the solution of α-cyano-3-phenoxybenzyl 2-(4-chlorophenyl)-isovalerate rich in said Y-isomer using a solvent made of one or more solvents selected from alcohols, aliphatic hydrocarbons and alicyclic hydrocarbons, or a solvent containing one or more of these solvents.

38. A process according to either of claims 2 or 24, wherein said Y-isomer is crystallized from the solution of α-cyano-3-phenoxybenzyl 2-(4-chlorophenyl)isovalerate, or the solution of α-cyano-3-phenoxybenzyl 2-(4-chlorophenyl)-isovalerate rich in said Y-isomer using an alcohol as the solvent.

39. A process according to either of claims 2 or 24, wherein said Y-isomer is crystallized from the solution of α-cyano-3-phenoxybenzyl 2-(4-chlorophenyl)isovalerate, or the solution of α-cyano-3-phenoxybenzyl 2-(4-chlorophenyl)-isovalerate rich in said Y-isomer using a solvent made of a mixture of an alcohol with one or more solvents selected from aliphatic hydrocarbons, alicyclic hydrocarbons and aromatic hydrocarbons.

40. A process according to either of claims 3 or 24, wherein said Y-isomer is crystallized from the solution of α-cyano-3-phenoxybenzyl 2-(4-chlorophenyl)isovalerate, or the solution of α-cyano-3-phenoxybenzyl 2-(4-chlorophenyl)-isovalerate rich in said Y-isomer using a solvent made of one or more solvents selected from alcohols, aliphatic hydrocarbons and alicyclic hydrocarbons, or a solvent containing one or more of these solvents, said solvent containing not more than 5% by weight of acetic acid on the basis of the total amount of solvent used.

41. A process according to either of claims 3 or 24, wherein said Y-isomer is crystallized from the solution of α-cyano-3-phenoxybenzyl 2-(4-chlorophenyl)-isovalerate, or the solution of α-cyano-3-phenoxybenzyl 2-(4-chlorophenyl)isovalerate rich in said Y-isomer using an alcohol as the solvent that contains not more than 5% by weight of acetic acid on the basis of the total amount of the solvent used.

42. A process according to either of claims 3 or 24, wherein said Y-isomer is crystallized from the solution of α-cyano-3-phenoxybenzyl 2-(4-chlorophenyl)isovalerate, or the solution of α-cyano-3-phenoxybenzyl 2-(4-chlorophenyl)-isovalerate rich in said Y-isomer using solvent made of a mixture of an alcohol with one or more solvents selected from aliphatic hydrocarbons, alicyclic hydrocarbons and aromatic hydrocarbons, said solvent containing not more than 5% by weight of acetic acid on the basis of the total amount of the solvent used.

* * * * *